US009126175B2

(12) United States Patent
Lewis et al.

(10) Patent No.: US 9,126,175 B2
(45) Date of Patent: Sep. 8, 2015

(54) HIGH-THROUGHPUT SCREENING AND DEVICE FOR PHOTOCATALYSTS

(75) Inventors: Nathan S. Lewis, La Canada (CA); Jordan Katz, Berkeley, CA (US); Todd Gingrich, Columbia, MO (US)

(73) Assignee: California Institute of Technology, Pasadena, CA (US)

( * ) Notice: Subject to any disclaimer, the term of this patent is extended or adjusted under 35 U.S.C. 154(b) by 641 days.

(21) Appl. No.: 12/540,255

(22) Filed: Aug. 12, 2009

(65) Prior Publication Data

US 2010/0051478 A1     Mar. 4, 2010

Related U.S. Application Data

(60) Provisional application No. 61/188,856, filed on Aug. 13, 2008.

(51) Int. Cl.
*B01J 19/00* (2006.01)
*G01N 27/403* (2006.01)

(52) U.S. Cl.
CPC .... *B01J 19/0046* (2013.01); *B01J 2219/00378* (2013.01); *B01J 2219/00387* (2013.01); *B01J 2219/00533* (2013.01); *B01J 2219/00603* (2013.01); *B01J 2219/00612* (2013.01); *B01J 2219/00653* (2013.01); *B01J 2219/00659* (2013.01); *B01J 2219/00704* (2013.01); *B01J 2219/00747* (2013.01); *B01J 2219/00754* (2013.01); *G01N 27/403* (2013.01)

(58) Field of Classification Search
CPC ............ B01J 2219/00747; B01J 2219/00704; B01J 2219/00754; C01N 27/403
USPC ............ 204/407; 205/775; 250/214.1, 214 R; 136/249

See application file for complete search history.

(56) References Cited

U.S. PATENT DOCUMENTS 6,326,090 B1 * 12/2001 Schultz et al. .................. 506/22
6,527,930 B1 *  3/2003 Kounaves et al. ............. 204/434

OTHER PUBLICATIONS

Arai T., Konishi Y., Iwasaki Y., Sugihata, H., Sayama K. "High-Throughput Screening Using Porous Photoelectrode for the Development of Visible-Light-Responsive Semiconductors." Journal of Combinatorial Chemistry, vol. 9, pp. 574-581, published Jun. 19, 2007.*

Addressable Microelectrode Arrays: Characterization by Imaging with Scanning Electrochemical Microscopy Cynthia G. Zoski and, Nafeesa Simjee, Olivier Guenat and, and Milena Koudelka-Hep Analytical Chemistry 2004 76 (1), 62-72.*

* cited by examiner

*Primary Examiner* — Luan Van
*Assistant Examiner* — Louis Rufo
(74) *Attorney, Agent, or Firm* — Gavrilovich, Dodd & Lindsey LLP

(57) ABSTRACT

The disclosure relates to compositions, devices and methods for screening of photocatalysts for water-splitting.

8 Claims, 9 Drawing Sheets

HIGH-THROUGHPUT SCREENING AND DEVICE FOR PHOTOCATALYSTS

CROSS REFERENCE TO RELATED APPLICATIONS

This application claims priority under 35 U.S.C. §119 from Provisional Application Ser. No. 61/188,856, filed Aug. 13, 2008, the disclosure of which is incorporated herein by reference.

STATEMENT REGARDING FEDERALLY SPONSORED RESEARCH

The U.S. Government has certain rights in this invention pursuant to Grant No. DE-FG02-05ER15754 T-103913 awarded by The Department of Energy.

TECHNICAL FIELD

The disclosure relates to compositions, devices and methods for screening of photocatalysts for water-splitting.

BACKGROUND

Hydrogen as a clean chemical source is important. The splitting of water by the combination of photocatalysts and solar energy has drawn strong attention as one ideal process.

SUMMARY

Arrays of mixtures of aqueous solutions of metal ions have been quickly and quantitatively deposited onto conductive glass substrates using a commercially available inkjet printer. These metal solutions were then pyrolyzed to form mixed metal oxides. By this method, very large numbers of combinations of different metals can be formed easily at low cost. In addition, the disclosure provides a screening method to search for materials capable of driving fuel-forming photoelectrochemical reactions. The methodology includes an open-circuit potential measurement of the material which provides useful information not readily and rapidly available from photocurrent-only measurements. The approach is easily adaptable to a full array of photoelectrochemical characterization, such as current-voltage behavior, and even the spectral response, flat-band determination by capacitance measurements (Mott-Schottky analysis), and measurement of minority-carrier diffusion lengths.

The disclosure provides an inexpensive inkjet printing method for quantitatively producing mixed metal oxide semiconductors consisting of different metals (e.g., 1, 2, 3, 4, 5, 6, 7, 8, 9 or more different metals). The method allows for traditional screening of photocurrents but also for the measurement of photovoltages.

The disclosure provides a method of screening photocatalysts (e.g., mixed metal-oxides) for photoelectrolysis, comprising: exposing an array comprising a plurality of distinct regions of photocatalysts to light in an electrolyte buffer, wherein each of the plurality of regions is electrically insulated from each other region and wherein each region comprises a conductive lead in electrical communication with each region; measuring a photocurrent, photovoltage or a combination of photocurrent and photovoltage of the regions; identifying those regions having a desirable photocurrent or photovoltage; and determining the photocatalyst composition of the region having the desirable photocurrent or photovoltage. In one embodiment, the regions of the array are generated by dispensing drops of a photocatalyst (e.g., a metal) onto the surface of the support from a drop dispensing device, which device traverse the surface of the support, wherein at least a first region of photocatalyst (e.g., a mixed metal-oxide) in the array differs in a composition parameter of at least one other region in the array. In another embodiment, the composition parameter comprises the amount of a metal or the type of metal. In yet another embodiment, the mixed metal-oxide comprises a combination of a main group, transition, lanthanide, or actinide metal. In another embodiment, the drop dispensing device comprises a plurality of reservoirs each comprising a compositionally different metal or metal combination. In yet still a further embodiment, the drop dispensing device dispenses drops from at least two different reservoirs of the plurality of reservoirs at a substantially identical location on the substrate. In another embodiment, the array is heated to form a solid mixed metal-oxide phase. In yet another embodiment, the array comprises a substrate having a first surface and a second surface, wherein the first surface comprises an etched conductive surface. In a specific embodiment, the etch conductive surface comprises discrete conductive leads.

The disclosure also provides a device comprising: a substrate; a plurality of photocatalysts (e.g., photoconductive mixed metal-oxides) disposed on the substrate each of the plurality of photoconductive mixed metal-oxides address by a distinct conductive lead; a chamber comprising an electrolyte buffer; a light source; and a measuring apparatus, wherein the measuring apparatus is electrically coupled to the conducive leads and is configured to measure a change in voltage or current, the chamber configured to receive the substrate and wherein the light source illuminates one or more of the plurality of photocatalysts (e.g., such as photoconductive mixed metal-oxides).

The disclosure provides an array comprising a plurality of mixed metal-oxide regions, wherein each region is insulated from at least one other region, and wherein at least two regions of the plurality of regions comprise separate conductive leads in electrical.

The disclosure provides a method for making an array of mixed metal-oxides on the surface of a support, said method comprising dispensing drops of a metal onto the surface of the support from a drop dispensing device, which device traverse the surface of the support, wherein at least a first spot of the mixed metal-oxide in the array differs in a composition parameter of at least one other drop of a spot in the array and wherein the spots are dispensed onto an addressable conductive lead, each conductive lead and spot being insulated from at least one other lead and spot. In one embodiment, the composition parameter comprises the amount of a metal or the type of metal. In yet another embodiment, the mixed metal-oxide comprises a combination of a main group, transition, lanthanide, or actinide metal. In yet a further embodiment, the drop dispensing device comprises a plurality of reservoirs each comprising a compositionally different metal or metal combination. In a further embodiment, the reservoirs comprise a conductive ink. In yet another embodiment, the reservoir comprises a metallic ink. In one embodiment, the drop dispensing device dispenses drops from at least two different reservoirs of the plurality of reservoirs at a substantially identical location on the substrate. In yet another embodiment, the array is heated to form a solid mixed metal-oxide phase upon firing or heating. In still a further embodiment, the substrate comprises a conductive substrate. In a further embodiment, the conductive substrate has been etched to generate a plurality of addressable regions each having a conductive lead.

The disclosure also provides a substrate made by the foregoing method(s).

The substrate above can be further coupled to a measuring device.

The methods of the disclosure can further include data analysis software, remote transmitting devices and receiving devices.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
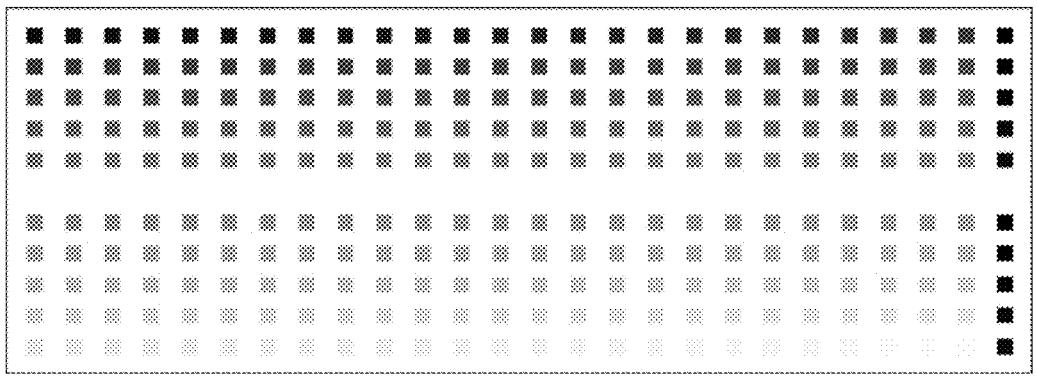
FIG. 1 shows a gray-scale TIFF image printed using the QTR software to make quantitatively predetermined mixtures of 255 different mixed-metal oxides on a single substrate. Rather than printing different images to generate different mixtures, the same TIFF file was used each time, but the QTR software used a new .quad file to generate the desired variation in elemental composition. The right-most column is composed of five controls that are five well-characterized materials with known open-circuit potentials.

As used herein and in the appended claims, the singular forms "a," "and," and "the" include plural referents unless the context clearly dictates otherwise. Thus, for example, reference to "a substrate" includes a plurality of such substrates and reference to "the metal" includes reference to one or more metals and equivalents thereof.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The development of highly efficient and light driven photocatalysts is needed for effective water splitting and other uses (e.g., $H_2O$ reduction, $CO_2$ reduction and the like). The main technical barrier is the vast number of possible combinations of photocatalyst materials (e.g., metal oxides, carbides, nitrites etc.) that must be produced and screened. In addition, once promising materials are identified it is quite challenging and time consuming to investigate the composition, band structure and morphologies of the material in order to configure it into a photoelectrode that can efficiently be used for the desired activity (e.g., photoelectrolyze water).

Several wide band-gap metal oxide semiconductors, such as $TiO_2$, $SrTiO_3$, and $KTaO_3$, have been shown to split water efficiently and to be chemically stable. However, these materials have band gaps of 3 eV or larger, and hence have relatively poor overlap with the solar spectrum at the surface of the earth. This poor spectral overlap results in these materials having overall solar energy-to-fuels conversion efficiencies of 1-2%. Other materials, such as CdTe or InP, have band-gaps that are better matched to the solar spectrum, but these semiconductors either corrode or develop electrically insulating overlayers when used as photoelectrodes in aqueous solution. Still other materials are stable and have band gaps relatively well matched to the solar spectrum, but do not produce photoexcited electrons with sufficient potential to reduce water to $H_2$ and/or photogenerated holes with sufficient potential to oxidize water to $O_2$.

One approach to expanding the set of suitable photoelectrode materials is to take a material that partially satisfies the spectral overlap, energetic, and stability requirements for water photoelectrolysis and attempt to modify the material so as to ameliorate its deficiencies. For example, the addition of Ni to $InTaO_4$ enhances the long-wavelength response of the material, producing photoactivity at wavelengths of light as long as 420 nm, although overall energy-conversion efficiencies in sunlight are still <1%. Similarly, many researchers have tried to develop chemical methods to passivate the semiconductor to prevent corrosion or degradation.

Current methods of screening are time consuming and complicated. For example, existing methods include creating a plurality of materials and subsequently equilibrating each of the individual materials, contacting each of the individual materials with light, mechanically changing buffers, illumination configurations, changing electrodes or combinations of all of the above. Using such methods, screening 10 different materials may take an hour or more.

The disclosure provides a high-throughput method of screening photocatalysts for a desired photocurrent or photovoltage. The method allows for simultaneous exposure of a plurality of regions comprising different materials to an electrolyte buffer comprising a counter electrode or reference electrode and illuminating the plurality of regions simultaneously. Measurements from each of the regions can be measured individually by closing and opening an electrical circuit for an addressable location comprising the region. In this way, the time associated for re-equilibrating, movement of electrodes and the like can be avoided and 10 different material compositions can be read/measured in seconds vs. minutes or hours.

Figure 3:
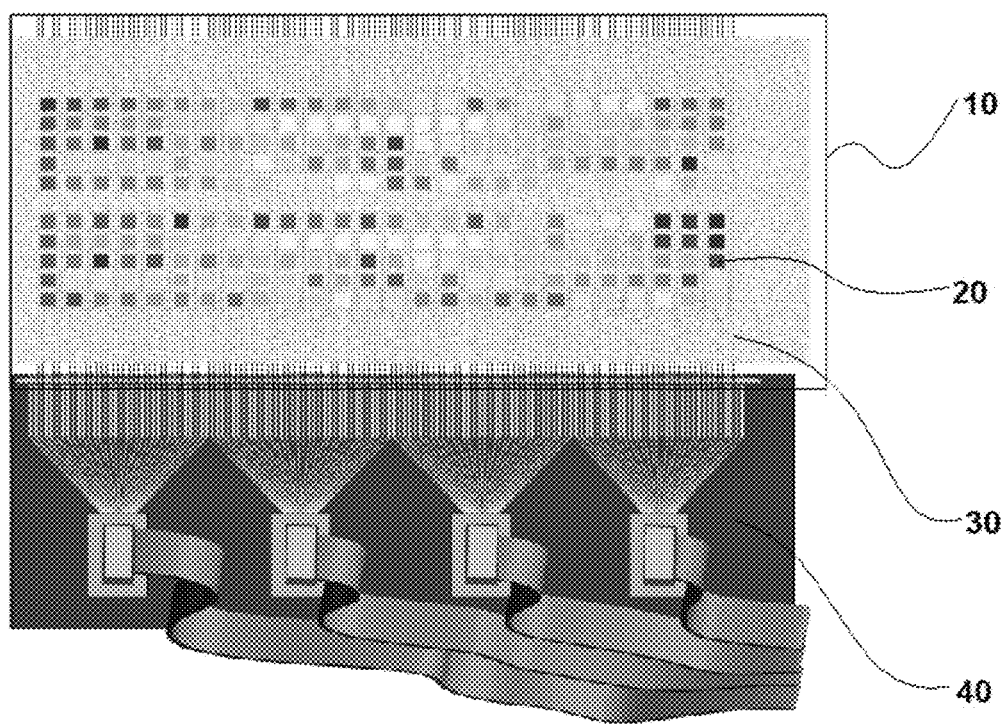
FIG. 3 Shows a schematic of a substrate comprising a plurality of addressable regions.

Referring to FIG. 3, one embodiment of the disclosure provides a substrate 10 comprising a plurality of addressable regions 20 having compositionally different materials, each of the regions electrically coupled to a conductive lead 30. The substrate comprises conductive leads useful for completing a circuit by coupling the leads 40 to a measuring device (further depicted in FIG. 5).

Figure 4:
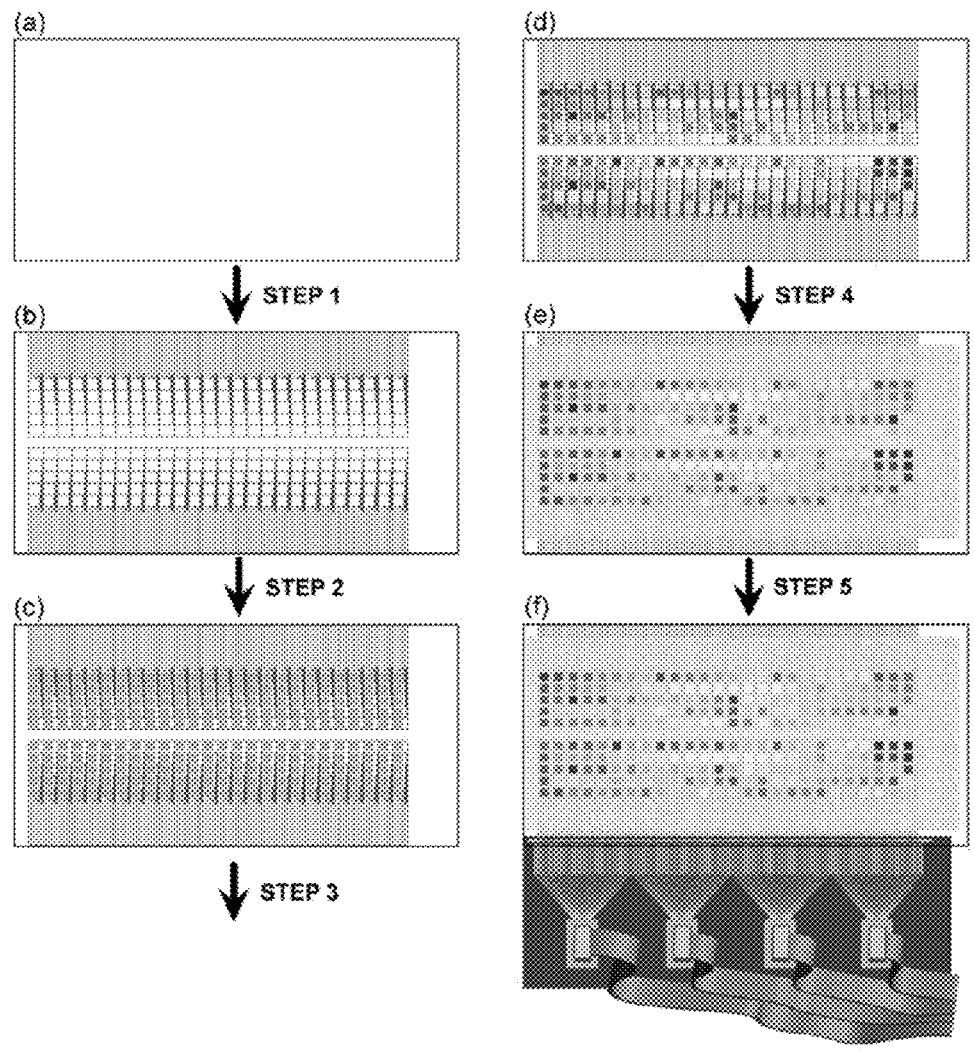
FIG. 4A-F shows a schematic of the process of preparing the substrate and making electrical contact to 130 individual materials on a single piece of FTO-coated glass. a) The substrate started as a sheet of glass uniformly coated with FTO. In Step 1, the FTO-coated glass was laser etched with a spot size of 50 μm. b) The etched FTO substrate, with 260 electronically isolated squares, with 130 contact pads along the two long sides of the substrate. In Step 2, the substrate was carefully cleaned and treated with siliconizing liquid for hydrophobicity, and aqueous solutions of metals were then printed using a commercial inkjet printer. c) After printing, the slide was dried at ~80° C. In Step 3, the substrate was baked at 500° C. for 3 h and cooled overnight, pyrolyzing the metal salts. d) After baking, mixed metal oxides of varying coloration were generated. In Step 4, the substrate was screen printed with a screen-printable epoxy, to passivate the surface area of the slide that was not covered by metal oxide spots. This step reduced the interfacial capacitive charging and minimized any deleterious electron-transfer processes that might occur at the FTO-water interface. e) In Step 5, electrical contact as made to each of the 130 contact pads along the edge of the substrate using an elastomeric connector clamped between a custom-made PCB with corresponding contact pads. f) Each contact pad on the PCB was routed to one of four ribbon cable connectors, which were subsequently connected to a second PCB.

The substrate 10 comprising the plurality of addressable regions 20 can be generated using a drop dispensing device. For example, as depicted in FIG. 4, a substrate (a) comprising a conductive layer is etched (Step 1) to provide a plurality of addressable locations each electrically connected to a conductive lead. A drop depositing device (e.g., an inkjet printer) can be used to deposit a test material at each addressable location to provides regions of a putative photocatalyst (Step 2). The substrate comprising the regions of material is pyrolyzed (Step 3) and an insulating epoxy screen-printed on the substrate (Step 4). The edge of the substrate comprising the conductive leads is then connected to a measuring device (Step 5). Ultimately, the substrate comprising the materials is submerged/exposed to an electrolyte solution and a light source wherein each of the regions can be selectively measured for a current or voltage or a combination thereof by closing a desired circuit associated with the addressable location.

The method includes dispensing combinatorial mixtures of metals onto a substrate. The substrate comprises addressable locations comprising a conductive lead. In one embodiment, the substrate can be an insulating substrate onto which a plurality of conductive leads has been deposited. In yet another embodiment, the substrate can comprise a conductive substrate that is etched to provide a plurality of conductive leads. Using either substrate, the conductive leads terminate at addressable locations. Each addressable location is then used to receive a drop (defining a region) of a mixed metal-oxide such that the region of mixed metal oxide can be individually measured if desired.

Combinatorial mixtures of metal oxides can be dispensed at the addressable locations using any number of methods. The size and/or density of the array of regions can be adjusted as desired. For example, a substrate can comprise at least 10, 20, 30, 40, 50, 60, 70, 80, 90, 100, 200, 300, 400, 500 or more addressable locations/regions of mixed metal-oxides on a substrate. It will be recognized that any number of integers in between the numbers above is contemplated by the disclosure.

In one embodiment, the disclosure provides a method of making an array of mixed metal-oxides. A specific embodiment of the method is depicted in FIG. 4. Referring to FIG. 4, a conductive substrate (such as an FTO-coated glass) is laser etched with a spot size of 50 μm (STEP 1). Step 1 provides an etched substrate, with a plurality of electronically isolated addressable sites with contact pads along the two long sides of the substrate. In Step 2, the substrate is cleaned and treated with siliconizing liquid for hydrophobicity, and aqueous solutions of metals were then printed using a commercial inkjet printer. After printing, the slide was dried at ~80° C. In Step 3, the substrate was baked at and cooled overnight, pyrolyzing the metal salts. After baking, mixed metal oxides of varying coloration were generated. In Step 4, the substrate was screen printed with a screen-printable epoxy, to passivate the surface area of the slide that was not covered by metal oxide spots. This step reduced the interfacial capacitive charging and minimized any deleterious electron-transfer processes that might occur at the conductive substrate-aqueous interface. In Step 5, electrical contact is made to each of the contact pads along the edge of the substrate. The array generated from the foregoing method can then be used in a device/system for quantifying the properties of the mixed metal-oxides (as described elsewhere herein).

For example, a high-throughput method is provided, using a commercial piezoelectric inkjet printer for synthesis and characterization of mixed-metal oxide photoelectrode materials for water splitting. The printer was used to deposit metal nitrate solutions onto a conductive glass substrate. The inkjet printer was used to deposit metal nitrate solutions onto a conductive glass substrate. The deposited metal nitrate solutions were then pyrolyzed to yield mixed-metal oxides that contained up to eight distinct metals. The stoichiometry of the metal oxides was controlled quantitatively, allowing for the creation of vast libraries of novel materials. Automated methods were developed to measure the open-circuit potentials ($E_{oc}$), short-circuit photocurrent densities ($J_{sc}$), and current density vs applied potential (J–E) behaviour under visible light irradiation. The high-throughput measurement of $E_{oc}$ is particularly significant because open-circuit potential measurements allow the interfacial energetics to be probed regardless of whether the band edges of the materials of concern are above, close to, or below the values needed to sustain water electrolysis under standard conditions. The $E_{oc}$ measurements allow high-throughput compilation of a suite of data that can be associated with the composition of the various materials in the library, to thereby aid in the development of additional screens and to form a basis for development of theoretical guidance in the prediction of additional potentially promising photoelectrode compositions.

The disclosure also provides combinatorial methods to synthesize new materials and characterize their photoelectrochemical properties using a high-throughput process of the disclosure. In one embodiment, a commercial piezoelectric inkjet printer is used to quantitatively combine up to eight different metal solutions at once, and the resulting mixture is then pyrolyzed to form mixed-metal oxides. The photoelectrochemical properties of these compounds are then determined in a high-throughput fashion by measurement of the open-circuit potential, $E_{oc}$, as well as the photocurrent. Measurement of $E_{oc}$ under high-intensity illumination provides a measurement of the majority carrier quasi-Fermi level under illumination, allowing compilation of a database of key photoelectrode performance properties associated with the materials of concern. In this fashion, the data can be used to guide secondary screens, to help formulate directions for new primary screens, and to form a basis for analysis by theory to guide exploration of additional sets of materials for desirable activity in photoelectrochemical solar-based water splitting.

In one embodiment, the disclosure provides a high-throughput method for screening mixed metal-oxides using a drop dispensing device comprising a plurality reservoirs each having a compositionally different metal or metal combinations. The dispensing device combinatorially combines drops on a substrate for generating a library of mixed metal-oxide materials. The disclosure provides that each region of a mixed metal-oxide comprises an addressable conductive lead. Such a method allows for the measure of not only current but voltage, a more effective measurement of mixed metal oxides for photocatalysts.

Aqueous metal nitrate solutions (e.g., Al, Cu, Co, Sr, Ni, Cr, Zn, Fe) and an aqueous titanium complex can be printed on a conductive glass surface using any number of drop dispensing devices. By "drop dispensing device" means any device that can dispense onto a substrate a nano-liter quantity of a fluid. The drop dispensing device can comprise a computer that can address the location of a drop on a substrate. In one embodiment, the substrate is located on a movable stage to allow movement of the substrate relative to the drop dispenser to provide drops and a desired location. In another embodiment, a drop dispenser of the device is moveable relative to a substrate to provide drops at a desired or selectable location on the substrate. For example, any number of different inkjet printers can be used in the methods of the disclosure. In one embodiment, a commercially available Epson Stylus Photo R800 was used. The metal solutions were printed in an array of spots, each containing controllable mixtures of the eight metals. These samples were dried then pyrolyzed at 500° C. yielding the associated metal oxide semiconductors.

It will be recognized that more than eight different metals can be used. In fact, a single metal containing ink can be used or the ink may comprise a plurality of metals thereby increasing the combinatorial mixed metal oxides that can be generated.

It will be recognized that the types of material to be applied to the substrate and screened do not have to be mixed metal oxides, but can be other materials suspected of having or having a photocatalyst activity. For example, the combinatorial screening techniques provided herein allow for rapid screening of mixed metal-oxides, nitrites, carbides and the like.

In one embodiment, a system for screening for a photocatalyst is provided. The system comprises an electrolyte buffer chamber. The buffer chamber can be used for simultaneous equilibrium and measurements of a substrate comprising a combinatorial array of photocatalysts and a counter electrode. The buffer chamber comprises a transparent portion for illumination of the substrate by a light source. In one embodiment, the array of photocatalysts is exposed simultaneously and continuously with a light source and each of the plurality of materials in the array is measured independently by modification of the circuit to the addressable location of the material. In one embodiment, the electrolyte buffer contacts all of the materials simultaneously and the buffer chamber comprising the array further comprises the counter electrode between which the voltage is measured and optionally a reference electrode.

Short-circuit current ($J_{sc}$) and open circuit voltage ($V_{oc}$) of the materials can be measured. For example, $J_{sc}$ measurements on binary metal oxides and $TiO_2$ controls demonstrated that some metal oxides could produce anodic photocurrents consistent with n-type materials while other materials generated cathodic photocurrents. Most notably, $TiO_2$ controls displayed strong photoanodic behaviour, while $Cu_{0.7}Zn_{0.3}O$ was shown to exhibit photocathodic behaviour. After one day of intense light exposure, however, $Cu_{0.7}Zn_{0.3}O$ stopped producing an appreciable photocurrent, suggesting that the current was actually due to a photocorrosion process. This observation highlights a major disadvantage to photocurrent screening; photocorrosion processes can result in false positives. Even more importantly, metal oxides under no bias will only exhibit significant photocurrents if the band edges are perfectly positioned to split water. If the conduction band edge is one-tenth of an electron volt too low in energy then the photocurrent will be essentially zero. It would be far more useful if the screen could identify such near misses.

Measuring the open circuit voltage ($V_{oc}$) provides a method to determine a rough approximation for the conduction band edge energy in photoanodes and the valence band edge energy in photocathodes. Thus by screening $V_{oc}$'s, near misses can also be identified.

Additionally, photocorrosion should not contribute to false positives in a photovoltage screen. By measuring the photovoltage, the composition can be probed to determine whether the majority carrier has sufficient free energy to drive the necessary chemical reaction at the surface of the metal oxide. A corrosion process can cause current to flow, but it cannot add to the free energy of the charge carriers, precluding the possibility of false positives. The disclosure demonstrates that measurements on $TiO_2$, $Cu_{0.7}Zn_{0.3}O$, and three other metal oxides demonstrate that the photovoltages are highly reproducible.

The methods presented herein improve significantly upon past high-throughput combinatorial screens of photocatalysts such as metal oxides. Materials can be rapidly produced with an inexpensive inkjet printer using multiple (e.g., up to eight or more) metals printed simultaneously and quantitatively. Additionally, the combinatorial measurement of $V_{oc}$'s allow a library of data to be collected rather than a library of hits or misses. From the library of $V_{oc}$'s qualitatively and quantitatively measurements can be obtained to analyze the effects of, for example, the mixed metals on the energetics of the band structure. Ultimately this will lead to more rational design of mixed metal oxides for solar hydrogen production.

For photoelectrochemical measurements, the substrate comprising the array of regions of photocatalysts (e.g., mixed metal-oxides) is submerged in an electrolyte solution except for a portion comprising the termination of the plurality of conductive leads. The substrate and a counter electrode may be submerged simultaneously in the same buffer and continuously illuminated. Illumination of the substrate can be made though a transparent window using an illumination device. Measurement of changes in current or voltage is transmitted from the substrate through the conductive leads to a measurement device. The measurement device is operably linked to a computer that can be used to perform any number of tasks including the quantifying and identifying those regions of mixed metal-oxide having a desirable current or voltage. The computer may also identify and output to a user the composition of the region having the desirable measurements. Individual regions on the array can be measured by modifying the open/closed status of the addressed region using the corresponding conductive lead on the substrate.

In a specific example, a FTO-coated glass substrate comprising an array of mixed metal-oxides is submerged in 1 M KOH(aq) (except for 1-2 cm at the top where electrical contact was made) and illuminated through a quartz window (GM Associates) by a 150 W Xe arc lamp. All measurements are made using LabView software, via a National Instruments BNC-2100 connector block and a PCI-6034E data acquisition card. The illumination intensity is measured with a Newport 815 power meter. As described below, the photoelectrochemical properties of the mixed-metal oxide materials are determined using either a photocurrent-only measurement system or using a system equipped to measure both the open-circuit photopotential and the short-circuit photocurrent.

In one embodiment, the array of mixed metal-oxides is contacted with light (e.g., visible light) to generate a detectable current or voltage signal. A detector detects the detectable signal from a plurality of regions or individual regions on the substrate and converts the detectable signal to a digital representation or fingerprint of the detectable signal from the array.

In one embodiment, the digital signal (i.e., digital data) is transmitted to a remote location. The digital signals (i.e., digital data) are then processed to detect and or characterize array data and identify a region or composition of a region having a desirable photocurrent or photovoltage. In one embodiment, a desirable mixed metal-oxide will comprise a band gap of at least 1.6-1.7 eV, but not over 2.2 eV.

The following examples are intended to illustrate but not limit the disclosure. While they are typical of those that might be used, other procedures known to those skilled in the art may alternatively be used.

EXAMPLES

Glass coated with fluorine-doped tin oxide (FTO) (Hartford Glass, TEC 15) was used as the substrate for the mixed-metal oxides. Prior to deposition of the metal solutions, the FTO-coated slides were washed thoroughly with soap and water, rinsed with distilled water and isopropanol, and dried under a stream of $N_2$ gas. The FTO was then treated with SurfaSil Siliconizing Solution (Pierce) to make the surface hydrophobic, and rinsed sequentially with isopropanol, water, and again with isopropanol, before being dried under a stream of $N_2$ gas. The metal nitrates $Al(NO_3)_3$, $Cu(NO_3)_2$, $Co(NO_3)_2$, $Ni(NO_3)_2$, $Sr(NO_3)_2$, $Cr(NO_3)_3$, $Fe(NO_3)_3$, and $Zn(NO_3)_2$ (all from Aldrich and ≥98% purity), and a water-stable titanium complex, titanium(IV) bis(ethyl acetoacetato)diisopropoxide (Tyzor LA, Aldrich), were used as received. The metal solutions for inkjet printing were made by dissolving sufficient metal salt into a base stock ink solution (MIS Associates) to produce 0.5 M metal ion concentrations. To improve the solubility of some of the metal salts, the base stock was first acidified with glacial acetic acid (Aldrich, >99.99%) to pH 4.5 for metal nitrate solutions and to pH 7.0 for Tyzor solutions. Electrolyte solutions for photoelectrochemical characterization consisted of 1.0 M KOH(aq) in >18.1 MΩ cm resistivity $H_2O$, obtained from a Barnsted Nanopure system.

A refurbished Epson Stylus Photo R800 piezoelectric inkjet printer (Epson.com) was used to deposit mixed-metal nitrate solutions directly onto a FTO-coated glass substrate. Instead of the standard eight ink cartridges, eight empty spongeless ink cartridges (MIS Associates) were each filled with a metal ion solution. A 2.3 mm thick high-density polyethylene (HDPE) template (Small Parts, Inc.) was cut to allow glass slides to be fed into the front of the printer using the CD-printing functionality.

The QuadTone Raster Image Processor software (QTR) (quadtonerip.com) was used to obtain quantitative control of the relative proportion of the printed metal solutions. QTR allows for user-defined control of how much ink is deposited from each cartridge. Using the QTR software, a file (a ".quad file") was used to define each gray-scale color so as to produce a specific volume of metal solution to be printed from each printer cartridge. A gray-scale tagged image file format (TIFF) image, with a maximum of 256 distinct gray-scale colors, was then printed (see FIG. 1). The same TIFF image was printed in each case, but each time using a different .quad file in QTR, resulting in a different mapping of the gray-scale color to the printed mixed-metal composition. In this way, a unique set of mixed-metal oxides was printed on each FTO-coated glass slide.

After being printed, the metal solutions were dried at 80° C. for ~30 min, heated under flowing air at 500° C. for 3 h, and then cooled to room temperature over ~8 h.

To ensure quantitative mixing of the aqueous metal solutions, the composition of mixed-metal oxide samples was characterized by energy dispersive spectroscopy (EDS) using a LEO 1550VP scanning electron microscope (SEM) equipped with an Oxford INCA 300 spectrometer. After pyrolysis, the printed thickness of the metal oxide samples was determined using a Dektak 3030 profilometer.

For photoelectrochemical measurements, a FTO-coated glass substrate was submerged in 1 M KOH(aq) (except for 1-2 cm at the top where electrical contact was made) and illuminated through a quartz window (GM Associates) by a 150 W Xe arc lamp. All measurements were made using LabView software, via a National Instruments BNC-2100 connector block and a PCI-6034E data acquisition card. The illumination intensity was measured with a Newport 815 power meter. As described below, the photoelectrochemical properties of the mixed-metal oxide materials were determined using either a photocurrent-only measurement system or using a system equipped to measure both the open-circuit photopotential and the short-circuit photocurrent.

Figure 2:
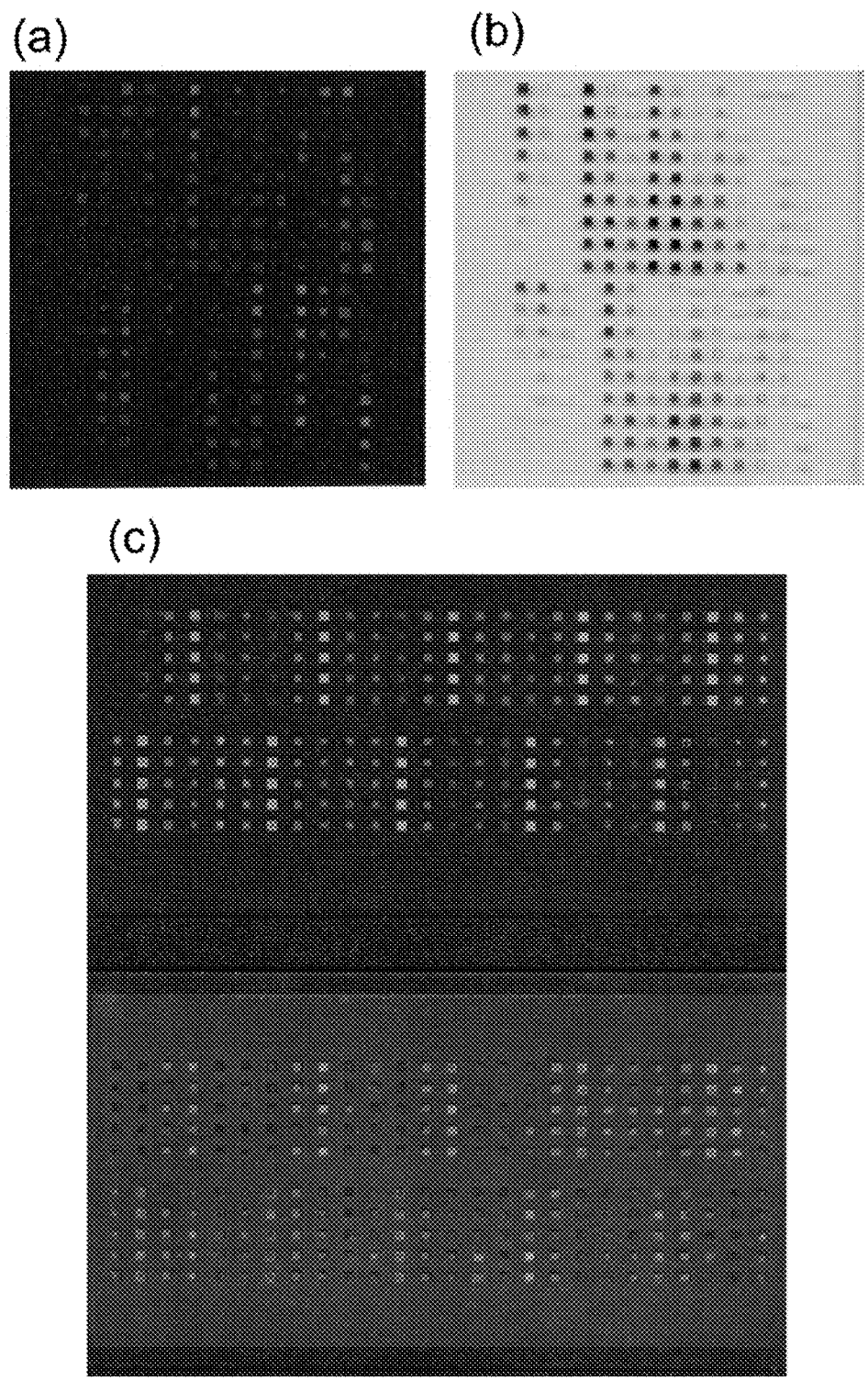
FIG. 2A-C show images of mixed-metal oxide spots printed on an FTO-coated glass substrate using an inkjet printer, which produced quantitatively predetermined mixtures of aqueous metal solutions that were then baked at 500° C. to form oxides. (a) and (b) Printed slides on a continuous FTO-coated glass substrate, as used for the photocurrent measurement setup. Panels (a) and (b) are images of the same slide, but a different background, for improved contrast in each image. (c) Image of the slide with a repeating pattern of five mixed-metal oxides. The upper image shows the slide after pyrolysis, and the bottom shows the slide after the FTO back-contact surface area had been coated with epoxy.
Figure 5:
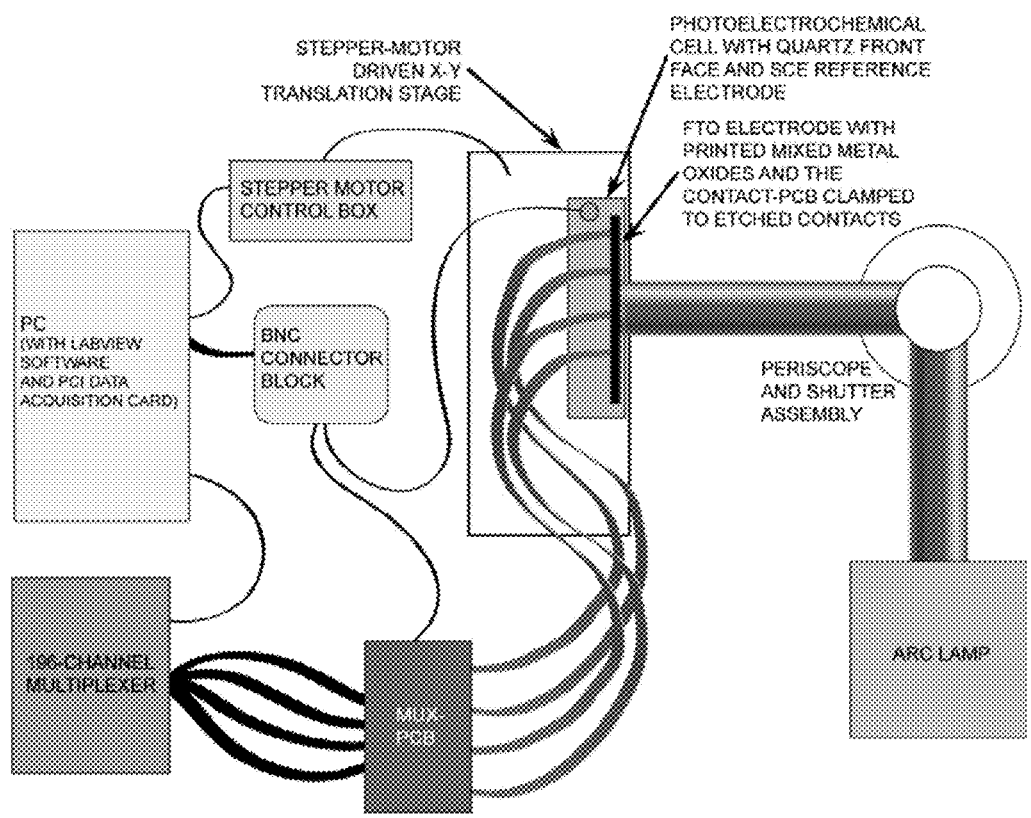
FIG. 5 shows a schematic of the experimental apparatus for combinatorial measurement of open-circuit potentials of mixed-metal oxides. The loosely focused output of a Xe arc lamp illuminated 10-15 printed spots at once. A motorized translation stage was used to keep the spots being measured in the region of maximum intensity as the materials on the slide were scanned from right to left. Each spot was electronically addressed individually via the contact-PCB, which was clamped to the etched FTO substrate. Four 34-wire ribbon cables were routed to the mux-PCB, which was interfaced with a computer-controlled 196-channel multiplexer.

To measure photocurrents, 252 unique metal oxides were printed on a 76 mm×102 mm rectangular FTO-coated glass slide. Typical printed slides of mixed metal oxides are shown in FIG. 2. In this configuration, a single electrical lead made contact to all of the metal oxides on a given FTO-coated glass slide, hence each material was in electrical contact with the other materials on the slide through the continuous, conductive FTO substrate. To address an individual metal oxide region, the output of the arc lamp was focused, using quartz optics, to a spot ~3-4 mm in diameter (FIG. 5). The beam was chopped at 13 Hz (CH-61, Boston Electronics). The photoelectrochemical cell was translated in the X-Z directions using a computer-controlled translation state (UniSlide translation stage, Velmex, Inc; MD-2 stepper-motor driver, Arrick Robotics; MD-2 LabView driver, TEM Consulting, LP). At each position of the translation stage, the photocurrent was measured, in a two-electrode configuration, with a Pt gauze counter-electrode, using a lock-in amplifier (EG&G 124A) equipped with a current-sensitive preamplifier (EG&G 184). A quartz slide split off ~10% of the intensity of the arc lamp beam, and the intensity of this beam was monitored with a Si photodiode to correct for any variation in the illumination intensity.

Photopotential Measurements.

For $E_{oc}$ measurements, each metal oxide material was electronically isolated from the other materials. In addition, the FTO back contact area was passivated to prevent the measurements from being dominated by the back-contact shunt that otherwise resulted from exposure of the conducting FTO to the electrolyte solution (FIG. 4). First, the FTO-coated glass slides were laser etched (50 µm laser spot size, Laserod, Inc.) to generate 260 electronically isolated conductive pads (4 mm by 3.8-5 mm) on each 77×152 mm FTO slide, with 130 contacts along each of the two 155-mm edges of the slide (FIG. 4b). After depositing and pyrolyzing the aqueous metal solutions, an insulating epoxy (1 part ADE678 and 5 parts ADE26, Nazdar) was screen-printed (using a HC-53 AMI Inc. screen printer, with a 255-40 mesh polyester screen and 12.7 µm of MX emulsion, Sefar Printing) over all of the exposed FTO to electronically passivate the regions of the FTO substrate that were not covered by the printed metal oxides (FIG. 4e). The epoxy was cured for ~30 min at 80° C., and was left for 5-7 days before use, to fully cure. Contact to each of the 1.0 mm center-to-center FTO contacts along the edge of the glass substrate was made using an elastomeric connector (Silver Zebra Series 5002 Solid Support, Fuji-Poly). The elastomeric connector was clamped, using two extended-reach clamps (McMaster Carr), between the substrate and a custom-designed printed circuit board (PCB) (Advanced Circuits), which had 134 1.0 mm center-to-center contact pads along one edge (FIG. 4f). Each contact pad of the clamped PCB (contact-PCB) was connected via a second PCB (mux-PCB) to the four 50-pin D-subminiature connectors of a National Instruments LHF200 switch cable, which was in turn connected to a 196-channel multiplexer (SCXI-1175, National Instruments) (FIG. 5). The open-circuit potential obtained from each spot was measured vs a saturated calomel reference electrode (SCE). To determine the effect of illumination relative to the equilibrium potential in the dark, the light beam was blocked for ~1 s, and the rise or decay in $E_{oc}$ was subsequently monitored.

Current-Density Vs Potential Measurements.

A nearly identical setup as that described for $E_{oc}$ measurements was used to measure the current-density vs potential behavior under potentiostatic control (SI 1287, Solartron) for mixed metal oxides. Measurements were performed vs a SCE at a scan rate of 20 mV s$^{-1}$ in a three-electrode setup with a Pt gauze counter electrode. Measurements were made both in the dark and under illumination.

Inkjet Printing.

A commercially available Epson R800 inkjet printer was used to quantitatively print mixtures of aqueous metal solution on glass substrates, with minimal modifications to the printer. A built-in printer functionality (designed to allow printing on CDs and DVDs) was used to print on rigid glass substrates. A simple HDPE template replaced the CD tray that is used to feed a CD into the printer. The template consisted of a rectangular (210 mm×300 mm) sheet of HDPE with a hole cut out of the center corresponding to the size of the FTO-coated glass substrate. Because of the method by which the printer senses the position of the loaded template when it is loaded, it was possible to easily print on the FTO substrate with very high reproducibility and spatial resolution (±0.5 mm).

A printer driver other than the Epson-provided driver was used to print mixtures with predetermined compositions. The QTR software allows the user to create a complete color-managed system for black and white printing. To print using QTR, a single TIFF image, consisting of 256 different gray-scale colors (see FIG. 1), was generated using Matlab. In a separate ".quad file," each color was uniquely defined in terms of a specific amount of solution to be dispensed from each of the eight printer cartridges. The same TIFF image was printed on each substrate, but a different .quad file was selected to create 255 new mixed-metal oxides, (the 256$^{th}$ gray-scale color was reserved for the area surrounding the spots, and thus always defined as printing nothing). A Matlab code automatically generated a set of .quad files so as to print every single possible combination of eight unique metals, in steps of 10% (by mole fraction). Upon changing one or more of the metals loaded in the printer, a new series of .quad files was subsequently generated, using a history of previously printed materials, to only generate mixtures that had not yet been printed, so as to avoid any repetition.

Determination of Metal Oxide Composition.

The composition of a test set of the printed spots was confirmed by EDS, after pyrolysis of the aqueous metal solutions at 500° C. Although the pyrolysis temperature is clearly a critical parameter in determining the crystallinity and/or phase of the resulting material, a maximum temperature of 550° C. is set by the stability of the FTO-coated glass.[13] A set of ~100 spots was tested, with the concentration of each metal in each mixture determined by the EDS INCA software, which calculates atomic percent compositions based on the acquired spectrum. Table 1 presents typical results from the compositional analysis of assorted metal oxide mixtures. In all cases, the elements present in the substrate were present in the EDS spectra. Only the elements specified in the quad file to be printed on a given spot were ever observed, except oxygen, silicon, tin, and calcium, which arose from the FTO-coated glass substrate.

TABLE 1

Representative values of the measured (by EDS) and expected elemental composition of binary mixed metal oxides. The expected value is given by the ratio of the volumes of metal ion solutions specified in the .quad file using the QTR software. The quoted errors are absolute composition errors.

| Measured | | Expected | | Error |
|---|---|---|---|---|
| % Fe | % Co | % Fe | % Co | |
| 0.58 | 0.42 | 0.70 | 0.30 | 12% |
| 0.51 | 0.49 | 0.60 | 0.40 | 9% |
| 0.41 | 0.59 | 0.50 | 0.50 | 9% |
| 0.32 | 0.68 | 0.40 | 0.60 | 8% |
| 0.24 | 0.76 | 0.30 | 0.70 | 6% |
| 0.15 | 0.85 | 0.20 | 0.80 | 4% |
| 0.06 | 0.94 | 0.10 | 0.90 | 4% |
| % Co | % Ni | % Co | % Ni | |
| 0.88 | 0.12 | 0.90 | 0.10 | 2% |
| 0.81 | 0.19 | 0.80 | 0.20 | 1% |
| 0.35 | 0.65 | 0.40 | 0.60 | 5% |
| % Cu | % Sr | % Cu | % Sr | |
| 0.31 | 0.69 | 0.40 | 0.60 | 9% |
| 0.23 | 0.77 | 0.30 | 0.70 | 7% |
| % Cu | % Cr | % Cu | % Cr | |
| 0.37 | 0.63 | 0.30 | 0.70 | 7% |
| 0.47 | 0.53 | 0.40 | 0.60 | 7% |
| 0.56 | 0.44 | 0.50 | 0.50 | 7% |
| % Co | % Cu | % Co | % Cu | |
| 0.41 | 0.59 | 0.40 | 0.60 | 1% |
| 0.49 | 0.51 | 0.50 | 0.50 | 1% |

For binary combinations of metals, the EDS analysis matched the expected percentage to within 5-10 percentage points (as much 15, but within 10 percentage points the large majority of the time). This accuracy should be sufficient for an initial screen of the metal oxide compositional space.

Photocurrent Measurements.

Figure 6A:
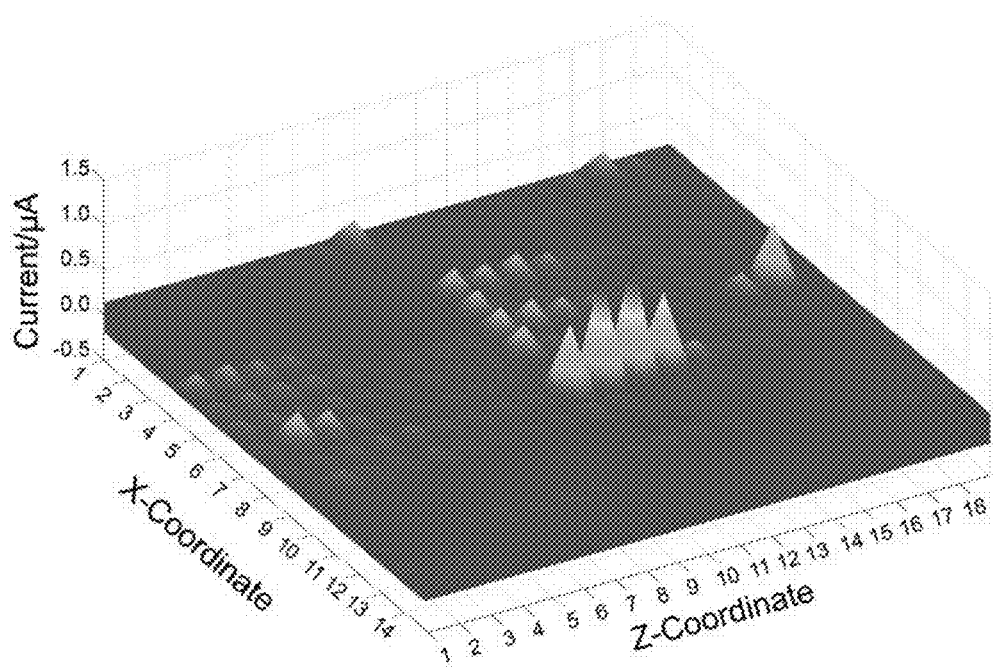
FIG. 6A-B is a false color images of the photocurrent of a slide that contained spots of binary mixed-metal oxides. a) Three-dimensional plot showing the physical position of each compound on the FTO substrate (X- and Z-coordinates correspond to the row and column of the spot, respectively) and the photocurrent measured for each spot. Positive values indicate a cathodic photocurrent. Column 15 and row 19 had nothing printed on them, and the bare FTO served as a control. b) Top-down view of the same data, with the composition of each spot superimposed on a false-color image indicating its visible (light blue spots-in particular in rows 11-12, column 11).
Figure 6B:
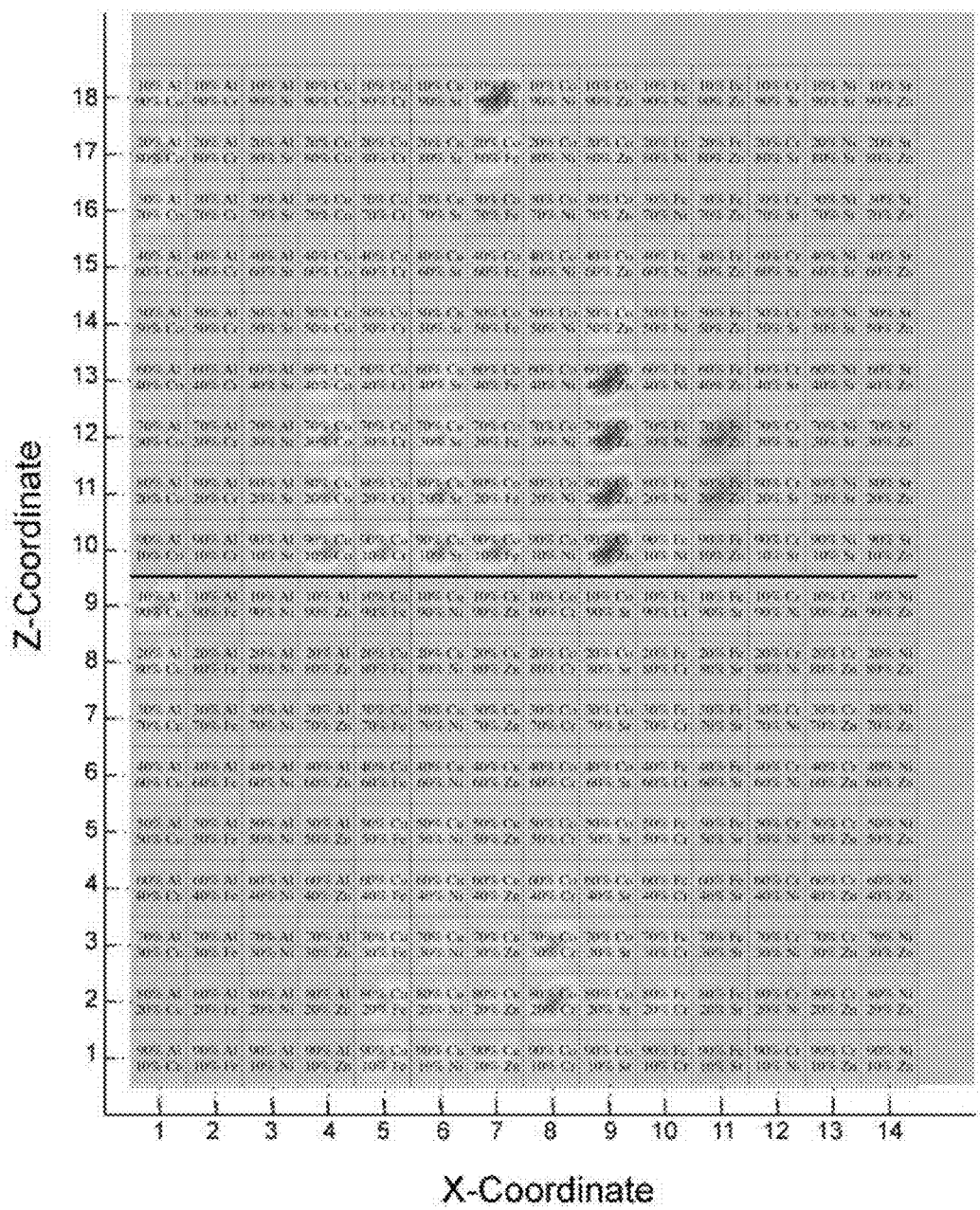

In the dark, a significant and varying current was measured at short circuit. The light source was thus chopped, allowing the AC effect of the light to be evaluated. The polarity of the photocurrent was indicative of whether the material exhibited photocathodic or photoanodic behavior. The photocurrent was measured for each spot for ~5 s, or until a stable value was obtained. FIG. 6 shows a false-color image of the photocurrent as a function of location on the FTO-coated glass substrate.

Initial measurements revealed a number of metal oxides that exhibited anodic or cathodic photocurrents having a magnitude between $10^{-9}$ and $10^{-6}$ A in the probed ~4 mm² printed spot area. While most materials tested gave no photoresponse at all, several binary combinations gave particularly strong photocathodic currents, including combinations of Co and Zn (80-20 and 70-30 percent Co and Zn, respectively), Co and Fe (90% Co and 10% Fe), and Al and Co (80% Co and 20% Al) (FIG. 6). For many materials, de-oxygenation of the electrolyte solution, by bubbling $N_2(g)$ through the cell, resulted in significantly increased photocurrents. Additionally, for several materials, the measured photocurrent changed over time. These changes included both increases and decreases in the magnitude of the photocurrent on the order of 50-100%, and occurred over a period of hours as well as from day to day.

Open-Circuit Potential Measurements.

Initially, the $E_{oc}$ of the mixed-metal oxides was measured in essentially the same way as the photocurrent. In this approach, illumination of individual materials on the slide was used instead of electronic isolation, but the light source was not chopped. However, even for well-characterized materials, the $E_{oc}$ values measured in this fashion were significantly more positive than expected. For example, for $TiO_2$, a potential of $-0.15$ V vs SCE was observed, but at pH 14, $TiO_2$ has a flat-band potential of $-1.1$ V vs SCE.[18] In addition, photoactive materials required as long as 30 min under illumination to exhibit a stable value of $E_{oc}$. The decay back to the equilibrium potential in the dark was even slower, thereby requiring nearly 12 h to scan a single slide that contained 252 materials (as opposed to <30 min for measurement of the photocurrents).

The combination of etching the FTO-coated glass substrate to electronically isolate the spots, and covering the FTO back contact area with epoxy, solved the issues with the low $E_{oc}$ values and the long apparent electrode response and recovery times. To electronically contact 130 individual spots on the etched FTO-coated glass electrode, a contact PCB, with a high density of metallic contact pads along one edge (as shown in FIG. 4f) was designed. An elastomeric connector was used to improve the conductivity of the connection, resulting in negligible contact resistance between the FTO and the contact PCB. To ensure that proper alignment was achieved each time, a resistance measurement was performed across two pairs of contacts on each end of the FTO-coated glass substrate.

Metal oxides printed on etched FTO substrates gave substantially faster response times, but the measured $E_{oc}$ still did not match the values expected for test materials, in particular for $TiO_2$. For $TiO_2$ at the same illumination intensity, $E_{oc}$ changed from $-0.81$ V to $-0.88$ V vs SCE by simply coating with epoxy the surrounding FTO substrate that was exposed to the electrolyte. Under strong illumination, the measured $E_{oc}$ of $TiO_2$ was within 200 mV of the reported flat-band potential for $TiO_2$ at pH 14. Finally, covering the edges of the sample with transparent epoxy resulted in $E_{oc}=-1.1$ V vs SCE for $TiO_2$.

Figure 7:
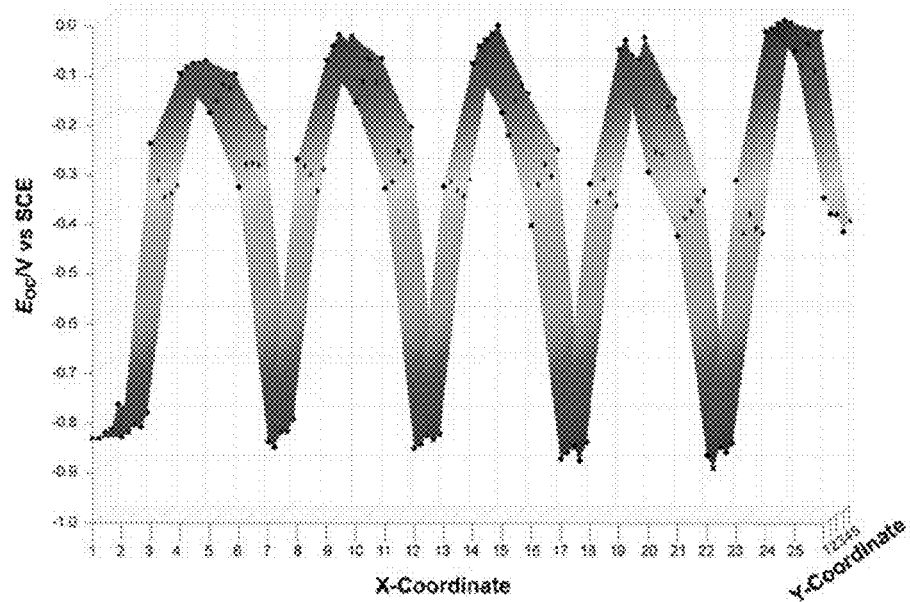
FIG. 7 shows open-circuit potentials for a control sample of mixed-metal oxides as a function of position on the FTO substrate. A photograph of the substrate itself is shown in FIG. 2c. A repeating pattern of five mixed-metal oxides was printed from left to right (with one extra column of $TiO_2$ at an x-coordinate equal to one). With each series of five columns (i.e., x-coordinates 2-6, 7-11, 12-16, etc.), the volume of aqueous metal solution inkjet that was printed varied from 30 to 62% of the maximum possible, resulting in material thicknesses from 180 nm to 420 nm. The open-circuit photopotentials were only weakly dependent the relative thickness of the printed oxide, and highly reproducible for nominally identical printed spots.

To test the overall measurement methodology, a repeating pattern composed of five materials was generated on a single FTO substrate (FIG. 2c). Each material was printed with five thicknesses (as controlled by changing the total volume of metal solution deposited by the printer), and each material was printed five times at each thickness value. FIG. 7 shows the $E_{oc}$ values recorded from this slide. Some variation was observed in $E_{oc}$ as a function of spot thickness, but spots with nominally identical compositions gave similar $E_{oc}$ values.

The $E_{oc}$ of the printed metal oxide materials in the dark varied greatly (values between $+0.2$ V and $-0.3$ V vs SCE were observed). This variation was not unexpected, because the solution potential is not well defined in the dark, but the variation introduced ambiguity in the determination of the polarity of the photocatalytic activity. Blocking the light beam briefly and measuring the shift in $E_{oc}$ from light to dark was used to verify the effect of illumination.

Figure 8:
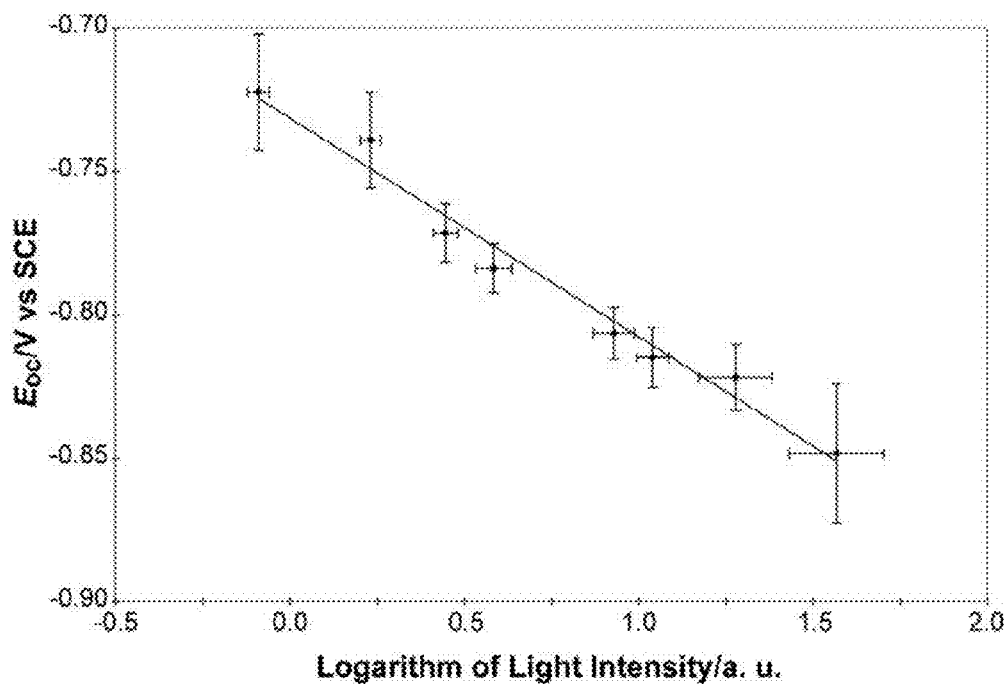
FIG. 8 shows a linear fit of the measured open-circuit potential vs the logarithm of the light intensity for $TiO_2$ samples. The slope of the fit was −76±12 mV per decade. The sign of the slope indicates that $TiO_2$ is a photoanode.

FIG. 8 shows a logarithmic dependence of $E_{oc}$ on the illumination intensity on a printed $TiO_2$ spot. The slope of a linear fit of $E_{oc}$ vs the logarithm of the illumination power was −76±12 mV per decade.

Current Density Vs Potential Behavior.

Figure 9:
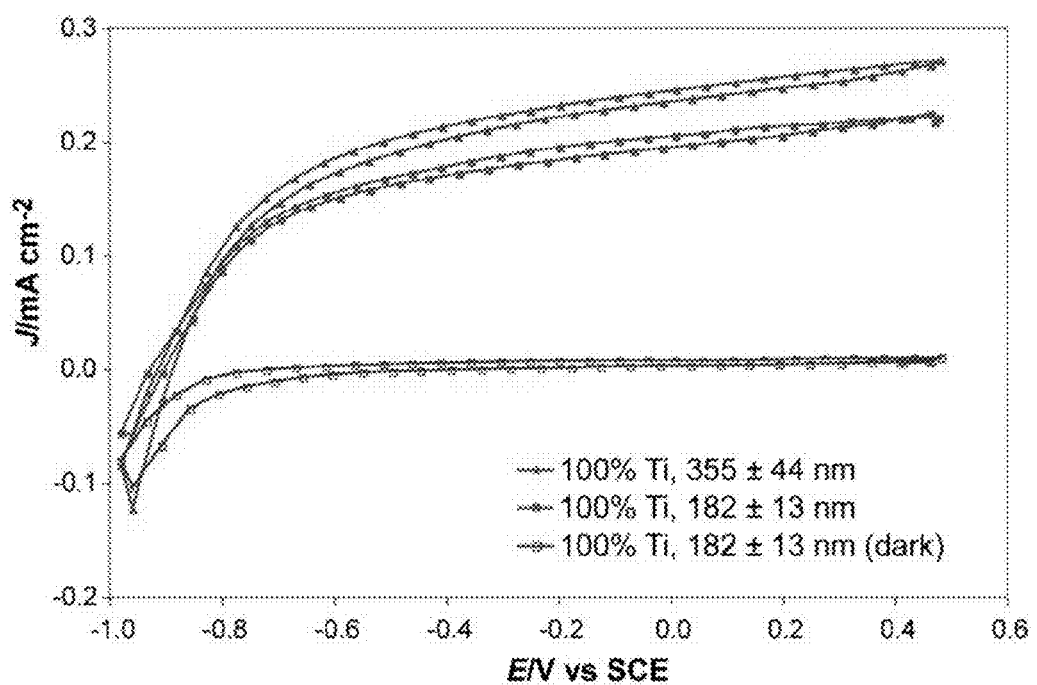
FIG. 9 shows J-E behavior of inkjet-printed $TiO_2$ on an etched FTO-coated glass substrate. The measured open-circuit potentials were the same, within the experimental error, as those measured by scanning J-E curves as well as by direct open-circuit measurements (although the J-E curves show non-negligible hysteresis). These measurements illustrate the flexibility of electronically isolating each material on the substrate, and also indicate that the volume of solution printed did significantly affect the measured photocurrent, but the open-circuit potential was relatively unchanged. Although the short-circuit current is in general a linear function of illumination intensity and of the light-harvesting ability of the material, the open-circuit potential has a much less sensitive, logarithmic dependence, on the light intensity. This means that day-to-day variability in light intensity or in a given material's optimal deposition thickness will have a minor affect on the open-circuit potential screening results.

The electronic isolation of each spot enabled combinatorial measurement of the complete current density vs applied potential (J-E) behavior of individual printed spots. FIG. 9 shows representative J-E data for samples of printed $TiO_2$ both in the dark and under illumination. The photocurrent of the $TiO_2$ showed a significant dependence on the amount of ink printed, with a maximum photocurrent observed for samples with an ink level of 46% of the maximum allowed by the QTR software, corresponding to a spot thickness of 355±44 nm. The $E_{oc}$ values measured by scanning J-E measurements corresponded closely to those measured directly at open-circuit. No significant effect was observed as a function of position of the spot in a given column on the slide, despite the varying resistivity of the connecting FTO "wire" (which varied from ~200 to ~1000Ω) due to the varying distance of the spot from the elastomeric connector.

Combinatorial synthesis and screening of novel mixed-metal oxide photoelectrodes has been demonstrated previously. The methodology described here affords several interesting capabilities. The first is the large number of metals that can be combined simultaneously during a single printing. The second is the information gleaned from an $E_{oc}$ measurement. The third is the flexibility in the types of photoelectrochemical measurements that can be made combinatorially and with high throughput.

One advantage of using the deposition method described herein is the very low cost for the entire printing system, which required no significant modification to a commercially available commodity ink jet printer. Using the QTR software, the printer provided accurate and reproducible deposition of solution volumes, allowing simultaneous control of both the spot composition and the total amount of material printed. This capability obviated the need to reprint a spot multiple times to increase the spot thickness, which in turn requires precise alignment of the substrate each time. Furthermore, the printer's eight ink cartridges allow a very large number of materials to be printed without changing the solutions in the printer, greatly decreasing the time required to print a library of mixtures consisting of three or more metals as compared to the printing time of a system that dispenses only one metal solution at time. The ability to load and use eight solutions simultaneously also minimized cross-contamination that could otherwise arise from the repeated printing of different solutions through a common set of printer nozzles.

Rather than producing a relatively smooth gradient of compositions, the system described herein used a quantized step size in elemental composition of the deposited metal salts. This step size must balance the need to fully explore the eight-dimensional compositional space while limiting the number of materials to synthesize and characterize in a preliminary compositional screen. For example, to prepare every possible combination of the eight metal solutions using a composition step size of 10% by mole fraction would require 78 FTO-coated glass slides each containing spots having 255 unique materials. If a promising material were found, the compositional parameter could be further optimized in a secondary screening step, to maximize the photoactivity.

Printing isolated spots of mixed-metal oxides provided several advantages relative to printing overlapping gradients. For photocurrent measurements, the relatively large spot-to-spot distance meant that the spatial resolution of the illumination source was not critical to the measurement, allowing the use of the focused beam of an arc lamp to provide intense white light excitation, rather than a continuous wave laser. Use of white light from an arc lamp is extremely versatile, in that its broad spectrum has significant intensity from 200 nm to 2500 nm. The use of a series of long-pass (or band-pass) optical filters in the beam path provides a simple, low-cost method for determining the wavelength dependence of the photoresponse of the metal oxides. Additionally, separation of printed spots relaxes the need for high spatial resolution for other methods of characterization (beyond the scope of this study), such as XRD, EXAFS or XANES, to determine phase, crystallinity or oxidation states.

The ability to generate photocurrent with a high external quantum yield (i.e., the fraction of electrons collected per incident photon) is an essential property of any efficient solar cell. However, the value of the photocurrent contains limited information as a criterion upon which to base a search for materials that can split water with visible light. Photocurrent can be generated by processes other than the desired water-splitting reaction, and conversely, a significant level of impurities in the material in the deposited spot could result in little or no photocurrent from an otherwise promising material.

In a combinatorial screening system, a significant percentage of false positives are time consuming and inconvenient, in that they prompt more detailed investigation of a material that is in the end unsatisfactory. The efforts to screen potential materials using only the photocurrent response resulted in a large number of such false positives. Conclusive determination of the origin of the photocurrent is at present far too time-consuming to be compatible with the high-throughput combinatorial approach of interest herein. In fact, the large majority of the photocurrents shown in FIG. 6 were ultimately deemed to be due to deleterious current-producing side reactions, rather than water splitting, as evidenced by the irreproducible magnitude of the photocurrent for these samples.

In addition to the inconvenience of false positives, photocurrent measurements fail to identify "near misses." If a material that very nearly satisfied all of the energetic and stability requirements for water photoelectrolysis were synthesized, and a low photocurrent was measured, that material would be discarded and perhaps never re-investigated. For example, failure to absorb a significant amount of light due a combination of a thin printed sample and a relatively low absorption coefficient could lead to a low photocurrent. Another mechanism to produce low photocurrents is if the material absorbs light and produces electrons and holes at the required potentials for water-splitting, but has very slow interfacial electron-transfer kinetics. Yet another possibility is that perhaps the material is ideal in all ways except that the potential of the bottom of the conduction band is just very slightly more positive than the hydrogen potential or the potential of the top of the valence band is very slightly more negative than the oxygen evolution potential.

Features of $E_{oc}$ Measurements.

An advantage of $E_{oc}$ measurements is that they reveal the position of the majority carrier quasi-Fermi level of the material under illumination. This value must be more negative than the $H_2O/H_2$ potential for a photoanode, or more positive than the $O_2/OH^-$ potential for a photocathode, to sustain the unassisted photoelectrolysis of water under standard-state conditions. The value of the majority carrier quasi-Fermi level thus reveals not only if a material is thermodynamically capable of splitting water, but if not, how close it is to doing so. In addition, if the material has band edges with sufficient potential to drive both half-reactions of water electrolysis, but a catalyst is necessary for the reaction to occur at an appreciable rate, the material would still be considered noteworthy in an $E_{oc}$ screen, but would likely be overlooked by screening only the photocurrent. Also, if for instance a photoanodic material had a conduction band-edge potential just slightly more positive than the $H_2O/H_2$ potential, this would be noted and further fine-tuning of the material's composition or morphology could potentially lead to the desired band-edge position.

$E_{oc}$ measurements also allow one to search for a complementary pair of photoanodes and photocathodes for water splitting. Rather than finding a single material that simultaneously satisfies all of the energetic and stability conditions for unassisted water photoelectrolysis, two light-absorbing materials can in principle be used in conjunction with each other. Such an approach changes two of the essential requirements: in a two-material case, the sum of the band-gaps of the materials must be >1.23 V, and the conduction band edge of the photocathode must be more negative than the $H_2O/H_2$ potential, while the valence band edge of the photoanode must be more positive than the $O_2/OH^-$ potential. Thus, by using two separate materials, the restrictions on viable materials are notably relaxed. Monitoring only the photocurrent, it is not possible to search individually for two materials that could drive each half-reaction when used together, since neither material would be capable of splitting water alone when used with a metallic counter-electrode.

Use of $E_{oc}$ Measurements to Differentiate Between Photocathodes and Photoanodes.

A number of proof-of-concept experiments were performed to test the photoelectrode screening system developed herein, using both an assortment of mixed metal oxides as well as the well-characterized photoanode, $TiO_2$. Using a kinetic model of interfacial electron transfer under illumination, the quasi-Fermi level of the material is expected to vary logarithmically with illumination intensity, by −59 mV per decade. This expectation is in accord with observations, as shown in FIG. 8. This behavior provides strong evidence that the measured $E_{oc}$ value is indeed determined by the quasi-Fermi level under illumination. Additionally, the sign of the slope indicates that $TiO_2$ is a photoanode, which agrees with the high-throughput method of deducing polarity from the direction of $E_{oc}$ drift immediately after the light source is blocked.

Although it is important to compare $E_{oc}$ at constant illumination for all samples, the logarithmic dependence ensures that $E_{oc}$ varies by less than 100 mV per order of magnitude change in intensity.[3] Variations in illumination intensity from spot to spot of more than a factor of two are very unlikely given the experimental setup. Furthermore, any photoanode that produces a majority-carrier quasi-Fermi level position under illumination within even 100-300 mV of the $H_2O/H_2$ potential would prompt further investigation. Preliminary screening of some 250 mixed metal oxides revealed no materials that produced $E_{oc}$ within 0.5 V of the $H_2O/H_2$ potential (except for $TiO_2$), and so choosing a relatively low threshold of $E_{oc}$ for screening materials may in fact be sufficiently selective for secondary study.

If $E_{oc}$ alone is measured, whether the material is a photoanode or photocathode response, or even photoactive at all, can in fact be ambiguous, due to the fact that there are two redox couples in solution with which the material can interact. Whether a material is photoactive is not always trivial to determine from $E_{oc}$ alone, because of the varying potential of different spots in the dark produced by the lack of a well-defined solution redox potential in electrolytes that lacked a rapid one-electron redox species. A material with $E_{oc}$=+0.2 V vs SCE would be considered a very good photocathode in the screening process, but if the dark potential was already at that value due to variations in the poorly defined solution potential and not due to a photoelectrochemical effect at all, the screening method would have actually returned a false positive.

For a large negative $E_{oc}$ value (e.g., $E_{oc}$<−1.1 V vs SCE), one might safely assume that the material is a good photoanode and that quasi-Fermi level is negative of the $H_2O/H_2$ potential. Similarly, a large positive $E_{oc}$ value (e.g., $E_{oc}$>0.2 V vs SCE) would indicate a good photocathode, with the majority-carrier quasi-Fermi level positive of the $O_2/OH^-$ potential. Intermediate $E_{oc}$ values are harder to interpret without further information. A material with $E_{oc}$=0 vs SCE might be selected as a reasonable candidate for further investigation if it was a photocathode. In contrast, a photoanode with such a positive $E_{oc}$ would be considered a very unsuitable material for water splitting. A third possible explanation is that the material could be inactive but the Nerstian potential of the cell in the dark happened to equal the potential of a SCE.

The sign of the slope of $E_{oc}$ vs the logarithm of the illumination intensity determines whether the material is photoanodic or photocathodic. However, making measurements for a full series of light intensities for each material is too time-consuming for a high-throughput approach. The sign of the slope is what is essential here, not the exact value of the slope itself, and so the simplest possible comparison of light intensities can be made quickly and easily: light vs dark.

The change in $E_{oc}$ after blocking the illumination source (or going from dark to light) is indicative of the photoelectrochemical nature of the material. A photoanode will produce a more negative $E_{oc}$ under illumination than in the dark, whereas a photocathode will produce a positive $E_{oc}$ shift under illumination. Thus, a determination can be made quickly for each material by briefly blocking the light source with a shutter and fitting any subsequent change in potential as a linear function (as a simple characterization rather than as a physical model for the decay time profile). A fit with a positive slope indicates a photoanode, one with a negative slope indicates a photocathode, and no change in $E_{oc}$ suggests that the material is not photoactive.

A number of embodiments of the invention have been described. Nevertheless, it will be understood that various modifications may be made without departing from the spirit and scope of the invention. Accordingly, other embodiments are within the scope of the following claims.

What is claimed is:

1. A device comprising
   a single transparent fluorine-doped tin oxide coated substrate that has been etched to generate at least fifty etched regions, wherein each etched region comprises an addressable conductive lead, and wherein the surface of the substrate comprising the etched regions is hydrophobic or has been treated to be hydrophobic;
   a plurality of photoconductive mixed metal-oxides disposed on the conductive leads;
   a layer of insulating epoxy applied to the surface of the substrate not covered by the mixed metal-oxides;
   a chamber comprising an electrolyte buffer;
   a light source; and
   a measuring apparatus,
wherein the measuring apparatus is electrically coupled to the conductive leads and is configured to measure a change in voltage or current, the chamber configured to receive the substrate and wherein the light source illuminates one or more of the regions of photoconductive mixed metal-oxides.

2. The device of claim 1, wherein the electrolyte buffer contacts all of the regions simultaneously.

3. The device of claim 1, wherein the electrolyte buffer comprises a counter electrode between which the voltage is measured and optionally a reference electrode.

4. The device of claim 3, wherein each electrode is contacted with an individual lead that is switched in and out between it and the counter electrode when the measurement is made.

5. The device of claim 1, wherein a light from the light source shines on all of the electrodes simultaneously.

6. The device of claim 1, wherein the light from the light source can be adjusted in space, intensity or in time of illumination.

7. An array comprising a plurality of mixed metal-oxide regions on a single transparent fluorine-doped tin oxide coated substrate, wherein each region is insulated from at least one other region, and wherein at least fifty of the regions of the plurality of regions comprise separate conductive electrical leads.

8. A substrate made by a method comprising dispensing drops of metal from a drop dispensing device onto an array of at least fifty etched regions comprising addressable conductive leads on a surface of a support where the device traverses the surface of the support so that each drop of metal is dispensed onto an addressable conductive lead, wherein at least a first etched region comprising a drop of metal in the array differs in a composition parameter to at least one other etched region comprising a drop of metal in the array, wherein each etched region comprising a drop of metal is insulated from at least one other etched region comprising a drop of metal, wherein the surface of the support comprising the array of etched regions is hydrophobic or has been treated to be hydrophobic, wherein a layer of insulating epoxy is applied to the surface of the substrate not covered by the drops of metals, and wherein the substrate is a single transparent fluorine-doped tin oxide coated substrate.

* * * * *